(12) United States Patent
Balog

(10) Patent No.: US 9,808,306 B2
(45) Date of Patent: *Nov. 7, 2017

(54) FUME EVACUATING ELECTROSURGICAL SCALPEL

(71) Applicant: Carl Balog, Portland, OR (US)

(72) Inventor: Carl Balog, Portland, OR (US)

( * ) Notice: Subject to any disclaimer, the term of this patent is extended or adjusted under 35 U.S.C. 154(b) by 634 days.

This patent is subject to a terminal disclaimer.

(21) Appl. No.: 14/308,552

(22) Filed: Jun. 18, 2014

(65) Prior Publication Data

US 2014/0303449 A1    Oct. 9, 2014

Related U.S. Application Data

(63) Continuation-in-part of application No. 13/587,859, filed on Aug. 16, 2012, now Pat. No. 8,784,416, which is a continuation of application No. 12/315,973, filed on Dec. 9, 2008, now Pat. No. 8,287,534.

(51) Int. Cl.
*A61B 18/14* (2006.01)
*A61B 90/30* (2016.01)
*A61B 18/00* (2006.01)
*A61B 18/12* (2006.01)

(52) U.S. Cl.
CPC .......... *A61B 18/1402* (2013.01); *A61B 90/30* (2016.02); *A61B 2018/00607* (2013.01); *A61B 2018/00922* (2013.01); *A61B 2018/00928* (2013.01); *A61B 2018/00946* (2013.01); *A61B 2018/00958* (2013.01); *A61B 2018/128* (2013.01); *A61B 2018/1412* (2013.01); *A61B 2090/306* (2016.02); *A61B 2218/008* (2013.01)

(58) Field of Classification Search
CPC .......... A61B 18/14; A61B 2018/00589; A61B 2018/00601; A61B 2018/00607
See application file for complete search history.

(56) References Cited

U.S. PATENT DOCUMENTS

| 4,562,838 | A  | * | 1/1986  | Walker  | A61B 18/1402 219/230 |
| 8,287,534 | B2 | * | 10/2012 | Balog   | A61B 18/1402 606/39  |
| 8,784,416 | B2 | * | 7/2014  | Balog   | A61B 18/1402 606/28  |
| 2010/0145333 | A1 | * | 6/2010 | Dethier | A61B 18/1402 606/42  |

* cited by examiner

*Primary Examiner* — Laura Bouchelle
(74) *Attorney, Agent, or Firm* — Ater Wynne LLP; Paul Heynssens

(57) ABSTRACT

An improved electrosurgical scalpel, with fume evacuation, for generating electrical signals intended for applications to the body of a patient via an electrosurgical electrode is provided that includes a channel to evacuate fumes generated. An electrosurgical scalpel includes a handle with a receptacle portion of a conductive hollow member for mounting and retaining an electrode blade and evacuating fumes, an optional light source with a power source that may be encapsulated within the handle and a vacuum port for applying a vacuum source to draw fumes away from the electrode tip through the chanel. Operation of a slide on the handle serves to retract or extend the electrode blade, and direct fume evacuation.

15 Claims, 12 Drawing Sheets

Internal view of fume evacuating electrosurgical scalpel with a removable blade
900

External view of fume evacuating electrosurgical scalpel with a removable blade
1000

Exterior side view of an example of a fume evacuating electrosurgical scalpel with a fixed blade
1100

FUME EVACUATING ELECTROSURGICAL SCALPEL

CROSS-REFERENCE TO RELATED APPLICATIONS

This is a continuation-in-part of application Ser. No. 13/587,859, filed Aug. 16, 2012; which is a continuation of Ser. No. 12/315,973 filed Dec. 9, 2008 the subject matter of which is incorporated herein by reference.

TECHNICAL FIELD

This description relates generally to diathermic instruments and more specifically to a disposable or reusable electrosurgical switch handle and a removable electrode blade including a mechanism for fume removal that is capable of supplying a high frequency current to a patient.

BACKGROUND

Various forms of diathermic surgical electrosurgical scalpels have been suggested and utilized in the medical field for a considerable period of time. These instruments have been utilized, for example, to burn or cut tissue. Generally, these instruments have utilized three different signals which are characteristically referred to as cutting signals, coagulation or hemostasis signals and a blend of signals or fulgurating signals which combine both the cutting and coagulation signals. These high frequency or radio frequency signals are generally applied to a patient by an electrode and conducted through the patient's body via a ground path provided by an electrode plate or indifferent plate that is maintained in contact with the patient's body. The application of the signals to the patient is through an electrosurgical electrode which applies the high frequency energy to a concisely concentrated point on the patient's body. The relatively large ground electrode plate provides an area for removing the applied energy without affecting the patient.

As is known, the actual cutting is accomplished by the concentrated application of high frequency electrical energy which effectively destroys the body cells directly beneath the electrosurgical electrode. The hemostasis or coagulation energy signals produce coagulation by the dehydrating or shrinking of the blood vessel walls around a contained clot of coagulated blood. This fusion or uniform coagulation of the blood vessel and its contents effectively seals off the flow of blood. Typically, such coagulation signals or pulses of energy have a dampened sinusoidal wave form.

Activation of the electrical signals to perform the cutting, coagulation or hemostasis is generally either by activation of a finger operated push contact button, finger operated push contact rocker switch or by foot controlled push contact button switches. The choice of the particular mode of operation of the electrosurgical instrument must frequently be accomplished with a minimum of diversion of the doctor from the site of surgery. In addition, the doctor must be able to maintain his hands on the switching handle that contains the electrosurgical electrode and be able to clearly see the site where the application of the electrode is applied. Finally, it is particularly desirable that the electrosurgical instrument be economically produced, so that it can be disposed after use, thus, insuring a new sterile instrument for each procedure.

It is the intention of the subject invention to provide a highly dependable electrosurgical switching handle, that is compatible with existing signal generators, with the addition of a light emitting source thereby directing light through a portion and out from the first and of the handle towards the distal end of the electrode to provide improved illumination to the concentrated application area around the electrode on the patient's body.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

The present invention provides an electrosurgical switching handle that is compatible with electrosurgical generator units for providing cutting and coagulation in the medical field and a method of manufacturing the same. The handle can be molded from plastic and includes a holding member for appropriate connection of electrical leads to a power supply capable of generating the desired radio frequency or high frequency electrical signals for cutting and coagulation; a holding member for appropriate connection of electrode for the application of electrical signals for cutting and coagulation; a light source, which could take the form of one or more light bulbs, or one or more Light Emitting Diodes (LEDs), and is electrically connected with a power source also encased within the handle such that neither the light bulb nor light power source are able to move relative to the handle; a switch externally accessible on the handle opens and closes the circuit between the light power source and light source to effectively energize and de-energize the light source as desired. In addition the handle includes a fume evacuation construction, so that fumes generated during use may be drawn away from the work area. This is typically provided by a tubular structure to which a vacuum is applied. The structure may include a design feature to allow extension of the tube and blade together.

Upon activation of the light by closing the circuit between the light power source and light source, light is directed out from the first end of the handle towards the distal end of the electrode.

In a first preferred embodiment the light power source is one or more batteries, with associated circuit, entirely encapsulated within the handle and isolated and independent from the high frequency electrical signal power supply. Accordingly, when the battery loses the charge, the light source no longer illuminates, however, the electrosurgical switching handle is still used the same as a conventional electrosurgical scalpel. In another preferred embodiment, an alternative, isolated light power source of indefinite life may be connected with the provision of a recharging port which is electrically connected with the light power source. The recharging port is specifically structured for electrical connection with a conventionally available battery recharging device for supplying an electrical recharging current to the light power source. Obviously, in this particular embodiment the light power source would be of a rechargeable type. In another preferred embodiment, the light power source is provided by tapping off available power from the high frequency electrical signal power supply within the handle and is electrically modified to be compatible with the light source and connected to the light source. In another preferred embodiment, an alternative external light power source of indefinite life may be connected with the provision of a connection port which is electrically connected with the light source. The connection port is specifically structured for electrical connection with a conventionally available external power supply device for supplying electrical current to the light source.

With the foregoing in mind it is the primary object of the present invention to provide a light emitting electrosurgical scalpel, which is extremely durable yet inexpensive to manufacture.

It is another object of the present invention to provide a light emitting electrosurgical scalpel which is specifically designed to protectively encapsulate a light source, light power supply and electrical conductors within the handle, thereby protecting the contents within the handle from damage due to shock, and maintaining an appropriately ergonomically designed and sized profile for ease of use by the doctors.

It is a further object of the present invention to provide a light emitting electrosurgical scalpel having a handle with a light source and rechargeable battery therein, the handle being provided with a recharging port for recharging the battery.

It is still a further object of the present invention to provide a light emitting electrosurgical scalpel having a light guiding shaft extending from a first end thereof and terminating at a distal end, wherein the electrosurgical scalpel is specifically designed to direct light through a solid light conducting medium from within the handle towards the distal end of the electrode.

It is a further object of the present invention to provide a light emitting electrosurgical scalpel having a handle with a light source with electrical connection to an external light power source, the handle being provided with a connection port.

The present invention both to its organization and manner of operation, together with further objects and advantages thereof, may best be understood by reference to the following description, taken in connection with the accompanying drawings and claims.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The examples below describe a fume evacuating electrosurgical scalpel. Although the present examples are described and illustrated herein as being implemented in a electrosurgical scalpel system including a light, the system described is provided as an example and not a limitation. As those skilled in the art will appreciate, the present examples are suitable for application in a variety of different types of electrosurgical scalpel systems, including those with differing lights, and even those without lights.

The following description is provided to enable any person skilled in the art of designing diathermic instruments to make and use the invention and sets forth the best mode contemplated by the inventors of carrying out their invention. Various modifications, however, will remain readily apparent to those skilled in the art, since the operation of the present invention has been described herein to provide an easily manufactured sterile electrosurgical switching handle instrument having a component part of an economical nature, so that the instrument is disposable after a single operation on a patient. Thus, the present invention has been optimized to insure the availability of a sterile electrosurgical instrument for every operation.

The electrosurgical switching handle apparatus of the present invention can removably mount an electrode for applying a high frequency electrical signal to biological tissue. The electrode can be powered from a high frequency generator capable of varying the power amplitude of the electrical signals. The doctor can select the desired frequency signal to provide either a cutting or coagulation operative mode. Various forms of high frequency current generators can be utilized along with various forms of electrode blades. With the electrosurgical instrument, a high frequency current will be applied to the tissue by way of an electrode having a relatively small cross section, so as to obtain a high current density at the operation site. Generally, an indifferent electrode which can take the form of a stainless steel plate is operatively connected to the patient and a conductive fluid can be applied to the patient to increase the contact area. It is highly desirable to provide for use with an electrosurgical unit, a disposable sterile switching handle assembly to minimize the possibility of infection.

Figure 1:
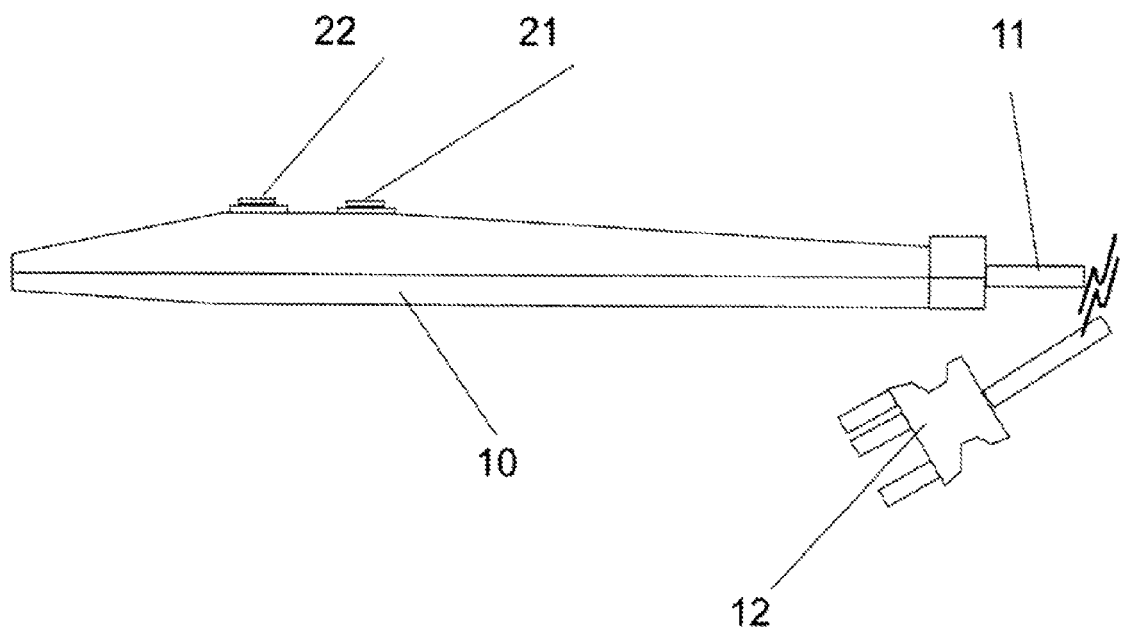
FIG. 1 is a side view of a conventional electrosurgical scalpel.

An example of an electrosurgical switching handle apparatus is depicted in FIG. 1.

Figure 2:
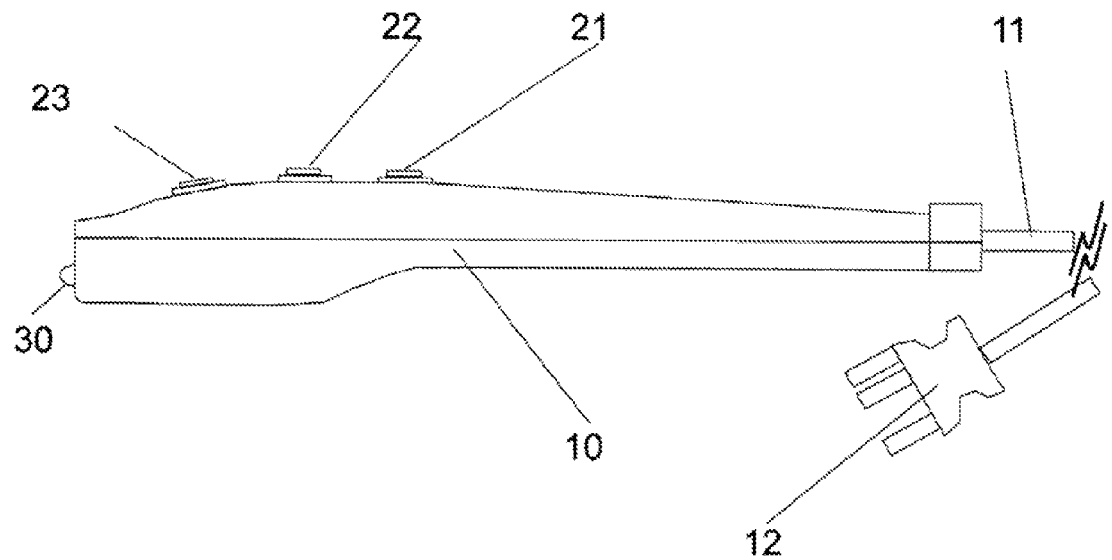
FIG. 2 is a side view of an electrosurgical scalpel according to a first embodiment of the present invention.

As shown in FIG. 2, an electrosurgical scalpel having a light emitting device according to the first embodiment of the present invention comprises a handle 10, electrical leads 11, terminating in a 3-pin plug 12, to a power supply capable of generating the desired radio frequency or high frequency electrical signals for cutting and coagulation, a light emitting device 30, a push button switch to activate cutting signals 22, a push button switch to activate coagulating signals 21 and a push button switch 23 to activate the light source. The handle 10 is made of durable plastic material with the light source projecting light through the front end of the handle.

Figure 3:
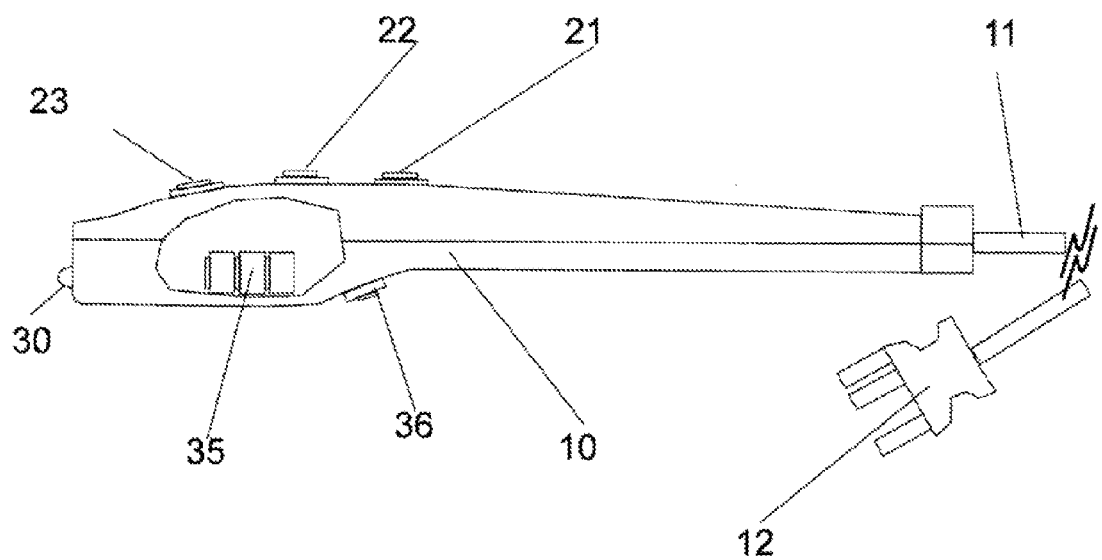
FIG. 3 is a side view of an electrosurgical scalpel, including a cutout view of the area accommodating the power source according to the second embodiment of the present invention.

As shown in FIG. 3, an electrosurgical scalpel having a light emitting device according to the second embodiment of the present invention comprises a handle 10, electrical leads 11, terminating in a 3-pin plug 12, to a power supply capable of generating the desired radio frequency or high frequency electrical signals for cutting and coagulation, a light emitting device 30, a push button switch to activate cutting signals 22, a push button switch to activate coagulating signals 21 and a push button switch 23 to activate the light source. The handle 10 is made of durable plastic material with the light source projecting light through the front end of the handle. Rechargeable batteries 35 are mounted within the handle and a recharging port 36 is provisioned within the handle to provide electrical connection with a conventionally available battery recharging device for supplying an electrical recharging current to the battery.

Figure 4:
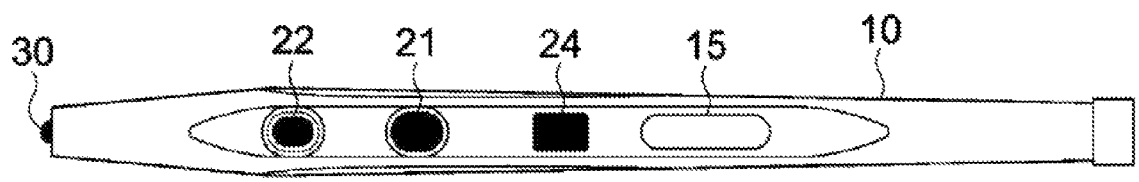
FIG. 4 is a top view, with exemplary dimensions in mm, of an electrosurgical scalpel according to the first embodiment of the present invention, with alternative positioning of switches.

As shown in FIG. 4, an electrosurgical scalpel having a light emitting device according to the second embodiment of the present invention comprises a handle 10, a light emitting device 30, a push button switch to activate cutting signals 22, a push button switch to activate coagulating signals 21 and a slide switch 24 to activate the light source. The handle 10 is made of durable plastic material with the light source projecting light through the front end of the handle. A molded recess 15 is provided for application of advertising logo and dimensions in mm provided for scaling indication.

Figure 5:
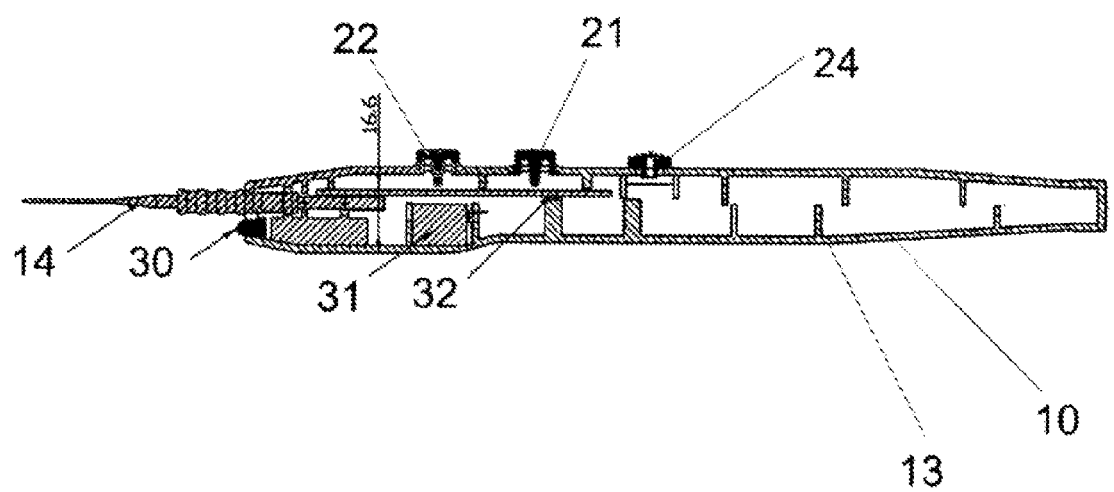
FIG. 5 is a cross-sectional view of an electrosurgical scalpel according to a first embodiment of the present invention, with alternative positioning of switches.

As shown in FIG. 5, an electrosurgical scalpel having a light emitting device according to the second embodiment of the present invention comprises a handle 10, a light emitting device 30, a push button switch to activate cutting signals 22, a push button switch to activate coagulating signals 21 and a slide switch 24 to activate the light source. The handle 10 is made of durable plastic material with the light source projecting light through the front end of the handle. Internal ribs 13 of suitable size and position provide the necessary internal support and guide paths for holding circuit board 32, batteries 31, electrode 14, and internal wire connections securely in position.

The electrosurgical switching handle assembly includes housing 10 which can have any desired configuration. In the preferred embodiment, the housing 10 is of a tubular shape and is opened at both ends. One end of the housing has a reduced neck portion for mounting a removable electrode blade 14. Preferably, the housing 10 is formed from an injection moldable plastic. Located in the top of the housing are switch buttons 22, 21, which are individually selected to supply high intensity (cut) or lower intensity (coagulation) signals to the electrode. Adjacent the top portion of the housing 10 is area for appropriate indicia, such as CUT and COAG which can be printed or molded on the exterior of the housing 10 adjacent the protruding button members 22 and 21. Buttons 22, 21 protrude freely down onto the circuit board 32 and the electrode 14, is mounted such that electrical connection is established between the electrode 14 and the circuit board 32.

An additional switch 24, is provisioned within the top of the housing 10, which is a single pole slide switch in this example. Electrical connections are provided by means of wire connections established between the positive side of the batteries 31 to one side of the switch 24, and the other side of the switch 24 to the positive terminal of the light source 30 (in this case an LED), with the return wire connection from the negative terminal of the light source 30 to the negative side of the batteries 31. Adjacent the top portion of the housing 10 is an area for appropriate indicia, such as ON and OFF which can be printed or molded on the exterior of the housing 10 adjacent the protruding switch member 24. Switch member 24 protrudes freely down into the housing allowing suitable electrical connection of the wire connections.

Figure 6:
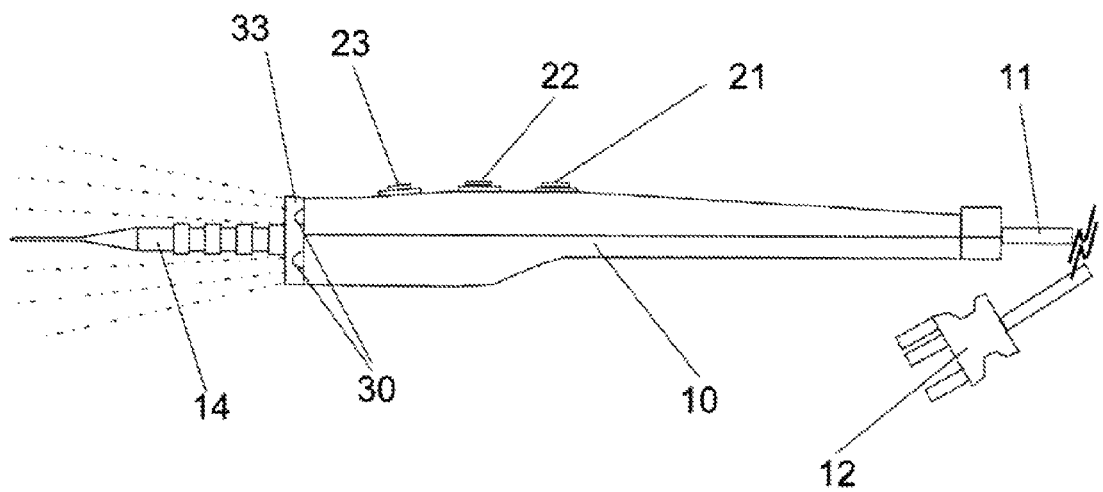
FIG. 6 is a side view of an electrosurgical scalpel, with optical lens arrangement illustrating light emission outwardly towards the electrode tip according to the first embodiment of the present invention.

As shown in FIG. 6, an electrosurgical scalpel having a light emitting device according to the first embodiment of the present invention comprises a handle 10, electrical leads 11, terminating in a 3-pin plug 12, to a power supply capable of generating the desired radio frequency or high frequency electrical signals for cutting and coagulation, a light emitting source comprising two light emitting elements 30, a push button switch to activate cutting signals 22, a push button switch to activate coagulating signals 21 and a push button switch 23 to activate the light source. The handle 10 is made of durable plastic material with the light source projecting light through the front end of the handle. A lens 33 is made of transparent material so that light emitted by the light emitting devices 30 can pass through the front end portion thereof.

Figure 7:
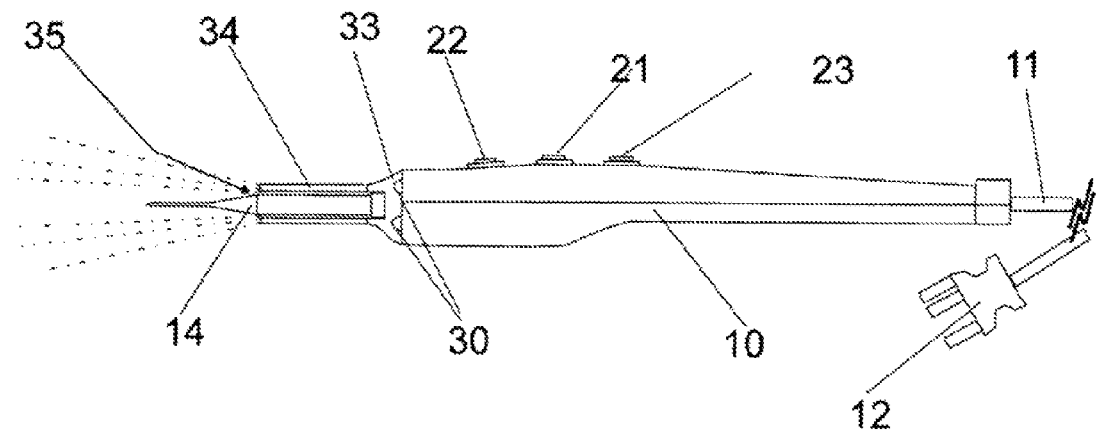
FIG. 7 is a side view of an electrosurgical scalpel, with optical lens arrangement including light guiding sleeve with illustration of light emission outwardly towards the electrode tip according to the first embodiment of the present invention.

As shown in FIG. 7, an electrosurgical scalpel having a light emitting device according to the first embodiment of the present invention comprises a handle 10, electrical leads 11, terminating in a 3-pin plug 12, to a power supply capable of generating the desired radio frequency or high frequency electrical signals for cutting and coagulation, a light emitting source comprising two light emitting elements 30, a push button switch to activate cutting signals 22, a push button switch to activate coagulating signals 21 and a push button switch 23 to activate the light source. The handle 10 is made of durable plastic material with the light source projecting light through the front end of the handle. A lens 33 is made of transparent material so that light emitted by the light emitting devices 30 can pass through the front end portion thereof. The light guiding sleeve 34 is made of transparent plastic material and is a hollow tube of a proper length. The light guiding sleeve 34 has a through hole 35 therein corresponding to the shape of the electrode 14. The electrode 14 is sleeved in the through hole 35 of the light guiding sleeve 34. The rear end of the light guiding sleeve 34 abuts tightly against the front end of the lens 33, and the front end thereof extends to be near the tip of the electrode. Thereby, an electrosurgical scalpel having a light emitting device according to the present invention is formed.

Figure 8:
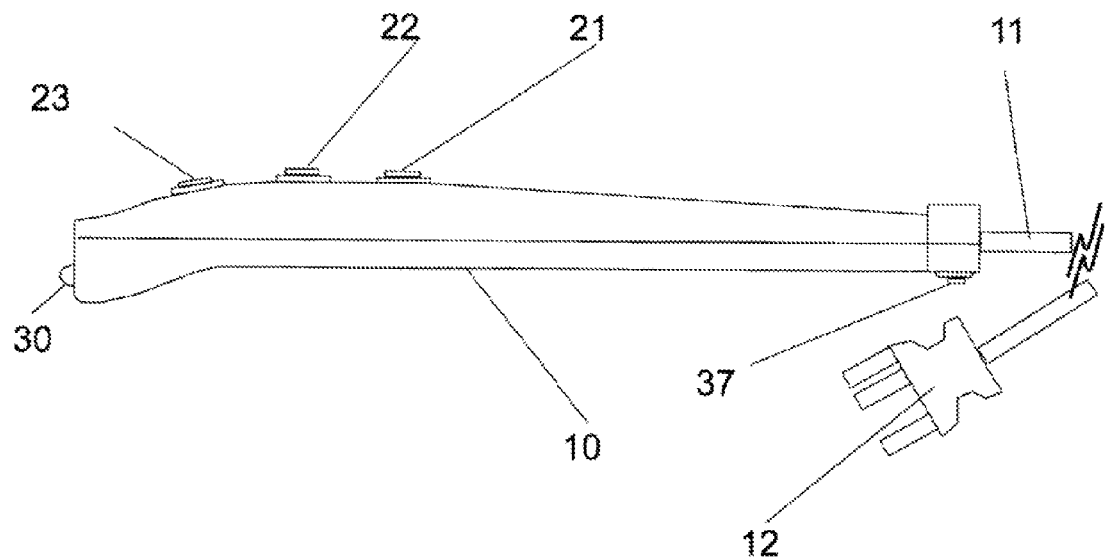
FIG. 8 is a side view of an electrosurgical scalpel, including a connection port to an external light power source according to the first embodiment of the present invention.

As shown in FIG. 8, an electrosurgical scalpel having a light emitting device according to the first embodiment of the present invention comprises a handle 10, electrical leads 11, terminating in a 3-pin plug 12, to a power supply capable of generating the desired radio frequency or high frequency electrical signals for cutting and coagulation, a light emitting device 30, a push button switch to activate cutting signals 22, a push button switch to activate coagulating signals 21 and a push button switch 23 to activate the light source. The handle 10 is made of durable plastic material with the light source projecting light through the front end of the handle. A connection port 37 is provisioned within the handle to provide electrical connection with a conventionally available external power supply for supplying an electric current to the light source, there being no light power source included within the main body of the electrosurgical scalpel device.

Figure 10:
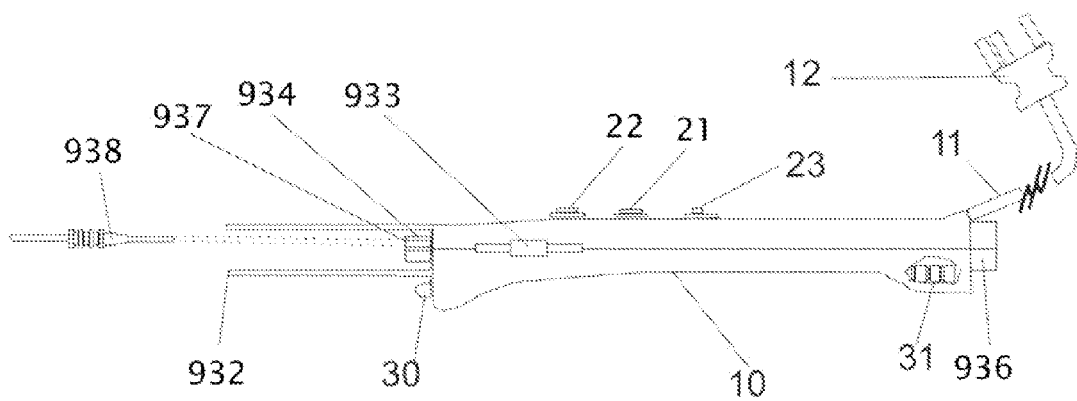
FIG. 10 is an exterior side view of an alternative example of a fume evacuating electrosurgical scalpel including a removable tip.
Figure 11:
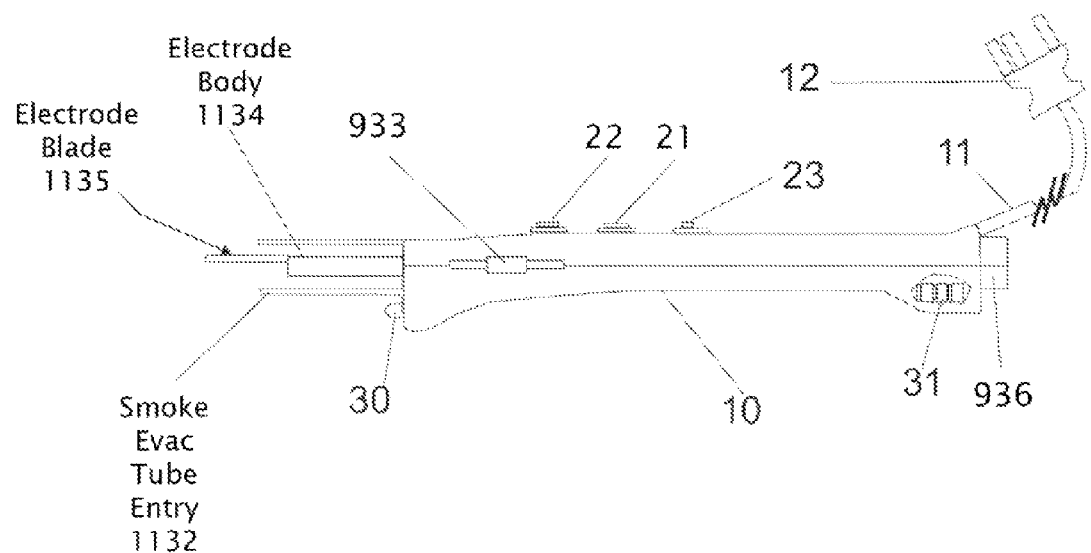
FIG. 11 is an exterior side view of an example of a fume evacuating electrosurgical scalpel with a fixed blade that extends and retracts.

The light is an aid to the operator, but sometimes the operators view of what is being done may be obscured, even with the aid of a light. During use the electrosurgical scalpel may emit fumes or smoke that interferes with the operator's vision. Accordingly, an example of the electrosurgical scalpel has been devised that typically allows such fumes to be removed, further aiding the operator, and is shown in FIGS. 9-11.

Figure 9:
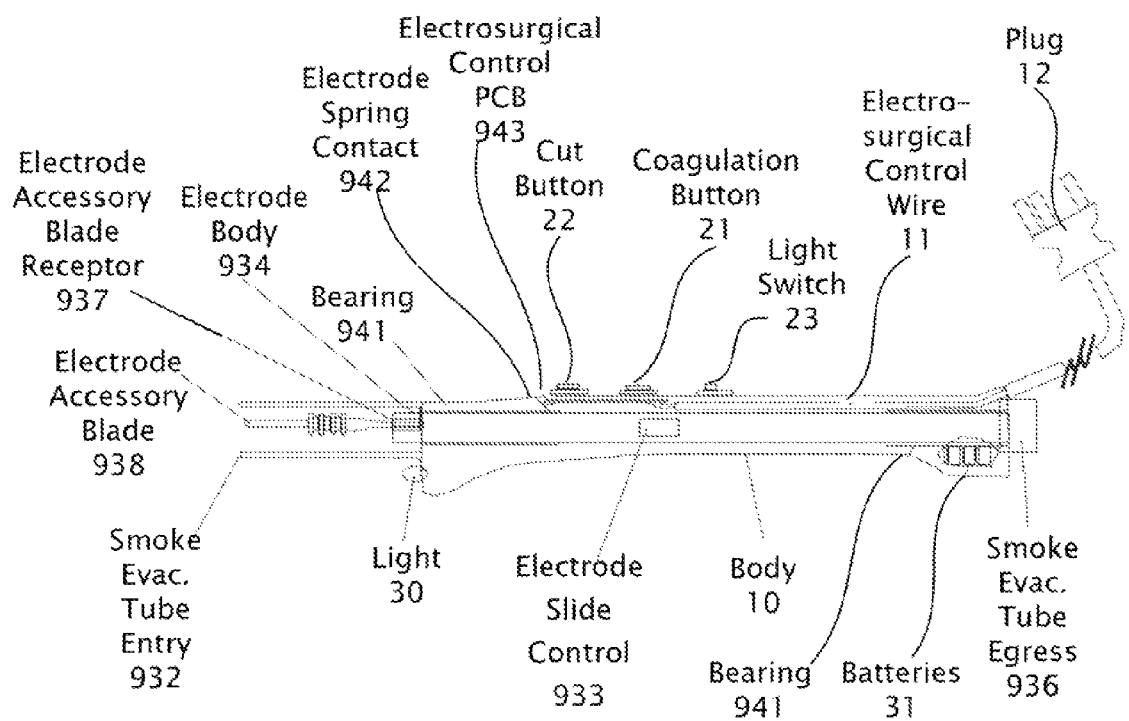
FIG. 9 is a cut away side view of an example of a fume evacuating electrosurgical scalpel with a removable blade.

FIG. 9 is a cut away side view of an example of a fume evacuating electrosurgical scalpel with a removable blade 900. The following examples advantageously allow smoke to be evacuated from the work area. This example advantageously utilizes an electrode accessory blade 938 that may be removed from a socket or electrode accessory blade receptor 937.

The smoke is evacuated via a smoke evacuation tube entry 932, that channels the smoke to a pathway in the electrode body 934. The electrode body aside provides a generally tubular pathway to which a vacuum is applied via a connection for smoke evacuation tube egress 936. The electrode body may be made to allow extension of the electrode accessory blade 938, by an operator operating an electrode slide control 933. The electrode slide control typically pushes the electrode accessory blade 938 back and forth through one or more bearings 941.

The bearings 941 are generally coaxial tubes through which the generally tubular electrode body slides. The bearing tubes 941 may be made from metal, or any convenient material. A front bearing tube 941 disposed near the electrode blade assembly of the device is typically fixedly attached to the case, or body, 10. The second bearing 941 disposed near the plug 12 end of the housing 10, is also a coaxial tube structure, and in addition to providing a bearing surface provides a point of connection to a vacuum line connector, or smoke evacuation egress tube 936. Accordingly, the electrode body 934 may slide in the second bearing 941, and into the interior of the vacuum line coupled to the smoke evacuation tube egress 936.

The electrode slide control 933 is typically a knob or raised lever that may protrude through an aperture disposed in the body 10 to accommodate its movement. The slide control is typically electrically insulated from the electrode body 934 to which it is coupled. Insulation prevents conduction to an operator or surrounding objects during use since the electrode body is utilized to conduct the electrical signal to the electrode accessory blade 938.

An electrode spring contact 942 is typically slidably coupled to the electrode body 934, by spring bias to maintain contact as the electrode body 934 is extended or retracted. The spring contact 942 is fixedly attached to an electrosurgical printed circuit board ("PCB") 943 that provides electrical control of the fume evacuating electrosurgical scalpel. The PCB 943 is also coupled to plug 12 that provides signals for the blade 938 through the electrosurgical control wire or conductor 11. Cut switch, or button, 22, and coagulation switch, or button, 21 are also electrically coupled to the PCB 943 that provides the desired signals and their routing.

One or more lights 30 may optionally be provided to further aid the operator. The light shown, is an LED. However, in alternative examples laser light sources, incandescent bulbs or their equivalents may be utilized. In particular an alternative example of the scalpel provides light through fiber optics coupled from a power supply and light source external to the scalpel 900, typically through a fiber optic cable disposed on the scalpel 900. In the example shown the LED light 30 is activated by a switch 23 that couples and un-couples internal batteries 31 to the light 30 typically through a wired connection. In alternative examples, power for the light 30 may be provided externally, typically through the plug 12.

FIG. 10 is an exterior side view 1000 of an alternative example of a fume evacuating electrosurgical scalpel including a removable tip. This view shows the exterior of the case 10 with the slide switch 933 disposed in the case 10. The view also shows the electrode accessory blade 938 removed from the electrode accessory blade receptor 937. The electrode body 934 may advantageously be extended so that the blade may clear the smoke evacuation tube entry 932 when the blade is changed.

FIG. 11 is an exterior side view of an example of a fume evacuating electrosurgical scalpel 1100 with a fixed blade that extends and retracts. This example is constructed as previously described in FIGS. 9-10. However in this example the blade 1135 may be integral to, and formed from, the electrode body 1134. The electrode body is typically a somewhat thin metal tube, so to form a blade the tube may be cut away to leave a blade shaped protrusion, that may or may not be flattened to form the blade 1135. This eliminates the socket or blade receptor (937 of FIG. 9) and may allow for a larger tube aperture in the electrode body 1134 to evacuate smoke, as the previously described socket tended to restrict the tube opening.

Figure 12:
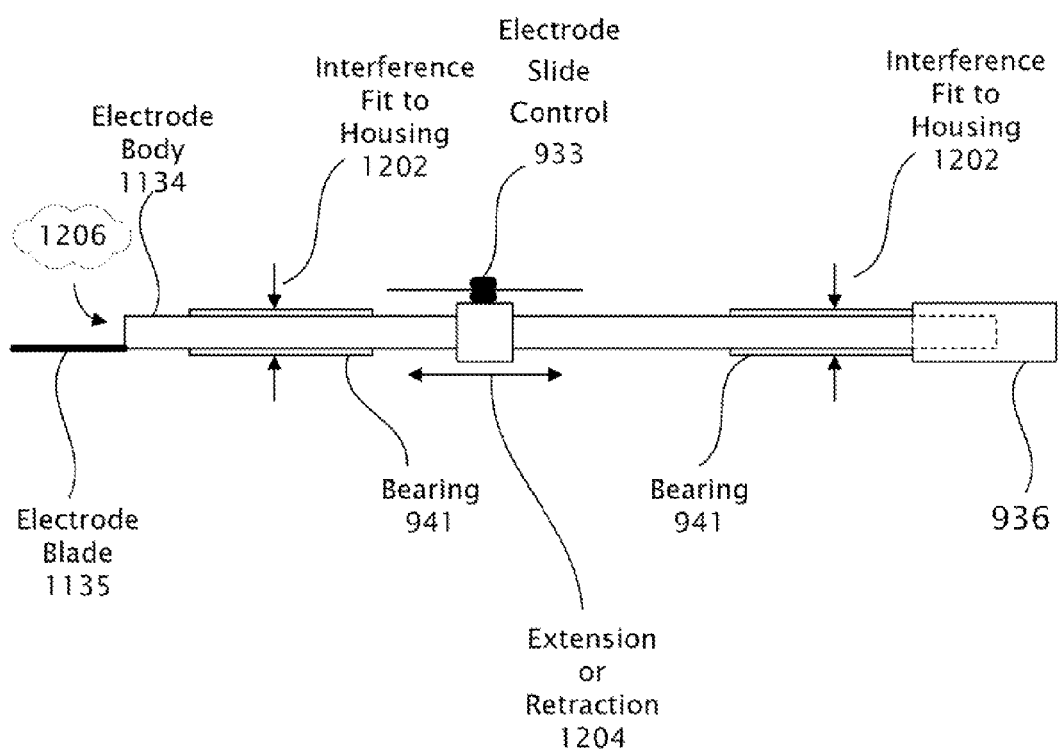
FIG. 12 is a detailed view of the mechanism that allows extension and retraction of the blade and smoke evacuation.

FIG. 12 is a detailed view of the mechanism that allows extension and retraction of the blade and smoke evacuation, of the example shown in FIGS. 9-11. In particular this example shows the blade configuration of FIG. 9. However, the construction applies equally well to the examples shown in FIGS. 9-10. The electrode blade 1135 is manufactured as part of the electrode body 1134, that also serves as a fume evacuation tube. Smoke 1206 is pulled into the electrode body 1134, which is a hollow tube, coupled to a smoke evacuation tube 936, which is in turn coupled to a conventional vacuum source (not shown). The tube, or body, 1134 is conductive metal and integrally formed with the electrode blade 1135 disposed at a first end.

A first end of the body 1134 fits inside a concentric metal tube that acts as a bearing 941. The fit is such that the bearing tube slides over the electrode body tube, but does not allow smoke to escape. An end of the bearing tube is coupled to a smoke evacuation tube egress fitting that supplies a vacuum to draw the smoke from the tube 1134. The vacuum device may draw the smoke away and vent it to the atmosphere, trap it, or route it to analytical or diagnostic equipment if desired. For example a mass spectrometer may be used to determine substances present in the smoke that may have diagnostic value. If the smoke is trapped, it may be filtered or otherwise processed so that it may be returned to the room atmosphere as clean air.

A second end of the body 1134 fits into a second bearing tube 941. This tube is also metal and fits similarly to the previously described bearing. This tube or bearing simply allows the electrode body to slide back and forth 1204. Both bearing tubes 941 are assembled into the housing (10 of FIG. 11) typically through an interference fit 1202 that keeps them stationary in the housing, but allows the electrode body 1134 to slide back and forth 1204. An electrode slide control 933 is fixedly coupled to the electrode body 1134, which allows an operator to extend or retract 1204 the electrode blade 1135.

Those skilled in the art will realize that the process sequences described above may be equivalently performed in any order to achieve a desired result. Also, sub-processes may typically be omitted as desired without taking away from the overall functionality of the processes described above.

Although the present invention has been described with reference to the preferred embodiments thereof, it will be understood that the invention is not limited to the details thereof. Various substitutions and modifications have been suggested in the foregoing description, and others will occur to those of ordinary skill in the art. Therefore, all such substitutions and modifications are intended to be embraced within the scope of the invention as defined in the appended claims.

The invention claimed is:

1. An electrosurgical instrument for selectively providing electrical energy to an electrode blade for cutting and coagulation, comprising:
    an elongate housing;
    a reduced neck portion at a first end of the housing, the neck portion being configured to retain an electrode blade extending outwardly therefrom, and the neck portion further including a tubular pathway to which a vacuum is applied to draw away fumes;
    a light source disposed within an interior of the housing;
    a light power source encapsulated within the interior of the housing;
    plural user-selectable switches disposed at least in part at an exterior of the housing, wherein:
        a first switch of the plural switches is configured, when actuated, to establish an electrically-conductive pathway between a retained electrode blade and an external electrosurgical signal generator, and
        a second switch of the plural switches is coupled in electrical communication with each of the light source and the light power source, wherein the second switch is configured, when actuated, to establish an electrically-conductive pathway between the light power source and the light source;
    a circuit board disposed within the housing and directly underlying at least one of the plural user-selectable switches, the circuit board further constituting a portion of the electrically-conductive pathway between the electrode blade and the external electrosurgical signal generator;
    a conductor including:
        a first end disposed within the housing and being coupled in electrical communication with the circuit board; and
        a second end extending outwardly from the housing and being configured for electrically coupling with the external electrosurgical signal generator;
        wherein either or both of the cutting signal and the coagulating signal comprises one of a radio frequency signal or a high-frequency electrical signal; and
    an electrode slide control lever, wherein the slide control is configured to: allow extension of the tubular pathway and maintain an electrically-conductive pathway between the electrode blade and an external electrosurgical signal generator.

2. The electrosurgical instrument of claim 1, wherein the tubular pathway and the blade are formed from a common tube.

3. The electrosurgical instrument of claim 1, wherein the tubular pathway is extendable.

4. The electrosurgical instrument of claim 1, wherein the first end of the housing includes a transparent lens configured to allow light from the light source to pass outwardly from the housing, and to channel fumes to the tubular pathway.

5. The electrosurgical instrument of claim 1, further comprising a tubular sleeve formed of a transparent, light-guiding material, wherein:
    the sleeve includes a proximal end abutting the first end of the housing and a distal end extending outwardly therefrom;
    the attached electrode blade and tubular pathway extends through a passageway within the tubular light-guiding sleeve; and
    a distal end of the electrode blade extends beyond the distal end of light-guiding sleeve.

6. An electrosurgical instrument for selectively providing electrical energy to an electrode blade for cutting and coagulation, comprising:
    an elongate housing;
    a reduced neck portion at a first end of the housing, the neck portion being configured to retain an electrode blade extending outwardly therefrom, and the neck portion further including a tubular pathway to which a vacuum is applied to draw away fumes;
    a light source;
    plural user-selectable switches disposed at least in part at an exterior of the housing, wherein:
        a first switch of the plural switches is configured, when actuated, to establish an electrically-conductive pathway between a retained electrode blade and an external electrosurgical signal generator, and
        a second switch of the plural switches is coupled in electrical communication with each of the light source and the light power source, wherein the second switch is configured, when actuated, to establish an electrically-conductive pathway between the light power source and the light source;
    a circuit board disposed within the housing and directly underlying at least one of the plural user-selectable switches, the circuit board further constituting a portion of the electrically-conductive pathway between the electrode blade and the external electrosurgical signal generator;
    a conductor including:
        a first end disposed within the housing and being coupled in electrical communication with the circuit board; and
        a second end extending outwardly from the housing and being configured for electrically coupling with the external electrosurgical signal generator;
        wherein either or both of the cutting signal and the coagulating signal comprises one of a radio frequency signal or a high-frequency electrical signal; and
    an electrode slide control lever, wherein the slide control is configured to: allow extension of the tubular pathway and maintain an electrically-conductive pathway between the electrode blade and an external electrosurgical signal generator; and wherein the light source comprises plural fiber optic elements coupled to an external light source, whereby light is conducted to a work area.

7. An electrosurgical instrument for selectively providing electrical energy to an electrode blade for cutting and coagulation comprising:
an elongate housing having a first end and an opposing second end thereof, wherein the first end includes a tubular assembly having a first tubular opening coupled to an electrode blade extending outwardly therefrom, and further including a tubular pathway to which a vacuum is applied to drawn away fumes;
a connection port disposed at an exterior portion of the housing, the connection port being configured to detachably couple with an external power source;
a vacuum port coupling to an external vacuum line and coupled to a second tubular opening of the tubular assembly;
a first switch disposed at an exterior portion of the housing and extending therethrough to an interior of the housing; and
a circuit board disposed within the housing and directly underlying either or both of the first and second switches, and further being configured, when the first switch is actuated, to affect an electrical circuit including the circuit board and an electrode blade coupled with the receptacle, respectively; and
an electrical conductor including:
a first end being coupled in electrical communication with the circuit board; and
a second end extending outwardly from the housing and being configured to electrically couple with an external electrosurgical signal generator;
wherein establishing an electrical pathway between the electrode blade, via a spring biased contact, and an external electrosurgical signal generator conveys to the electrode blade at least one of a cutting signal and a coagulating signal;
an electrode slide control lever, wherein the slide control is configured to:
allow extension of the tubular pathway and maintain an electrically-conductive pathway between the electrode blade and an external electrosurgical signal generator.

8. The electrosurgical instrument of claim 7 further comprising a light-emitting element mounted within the housing, the light-emitting element being positioned and configured, when illuminated, to directly light outwardly from the first end of the housing.

9. The electrosurgical instrument of claim 7, wherein the external power source and the external electrosurgical signal generator comprise a single power supply coupled with the electrosurgical instrument.

10. The electrosurgical instrument of claim 7, wherein the first end of the housing includes a transparent lens configured to allow light from the light-emitting element to pass outwardly from the housing through the first end.

11. The electrosurgical instrument of claim 10, wherein the housing further includes another light-emitting element disposed therein.

12. The electrosurgical instrument of claim 10, wherein a portion of the first end of the housing retaining the electrode blade is configured as a reduced neck portion.

13. The electrosurgical instrument of claim 7, wherein depressing the first switch causes a portion thereof extending within the housing to:
affect an electrical coupling with the underlying circuit board;
form an electrical circuit connecting the electrosurgical current generator and an electrode blade disposed in the receptacle; and
communicate from the electrosurgical current generator to the electrode blade either of a cutting signal or a coagulating signal.

14. The electrosurgical instrument of claim 13, further comprising a second switch wherein depressing the second switch causes a portion thereof extending within the housing to:
affect an electrical coupling with the underlying circuit board;
form an electrical circuit connecting the electrode blade and the electrosurgical current generator; and
communicate from the electrosurgical current generator to the attached electrode blade the other of an operable cutting signal or an operable coagulating signal.

15. The electrosurgical instrument of claim 14, further comprising a tubular sleeve formed of a transparent, light-guiding material, wherein:
the sleeve includes a proximal end abutting the first end of the housing and a distal end extending outwardly therefrom;
the attached electrode blade extends through a passageway within the tubular light-guiding sleeve; and
a distal end of the electrode blade extends beyond the distal end of tubular light-guiding sleeve.

* * * * *